United States Patent [19]

Kado et al.

[11] Patent Number: 4,663,162

[45] Date of Patent: May 5, 1987

[54] **METHOD OF USING *BACILLUS POLYMYXA* 9A TO PROTECT PLANTS AGAINST VERTICILLIUM WILT**

[75] Inventors: Clarence I. Kado; William C. Schnathorst; Hamid R. Azad, all of Davis, Calif.

[73] Assignee: The Regents of the University of California, Berkeley, Calif.

[21] Appl. No.: 589,606

[22] Filed: Mar. 14, 1984

[51] Int. Cl.[4] .................. A61K 39/07; C12R 1/12; A01N 63/00

[52] U.S. Cl. .................. 424/92; 424/93; 435/838; 71/77

[58] Field of Search .............. 424/92, 93, 435, 838

[56] References Cited

PUBLICATIONS

Ezrakh et al., Interaction of Bacteria with Pathrgenic Fungi . . . Verticillium, *Mikal* fitopathol. 13(4), 1979, pp. 283–286, (Abstracts).

Mikhaslova et al., Antagonist Action on Bacteria, . . . Cotton D. Wilt UZB Biol. ZH 14(3) 1970, 57–58.

*Primary Examiner*—John Kight
*Assistant Examiner*—Garnette D. Draper
*Attorney, Agent, or Firm*—Bertram I. Rowland

[57] ABSTRACT

Bacillaceae capable of inhibiting the growth of *Verticillium dahliae* have been found to protect agricultural crops against verticillium wilt. In particular, by applying *Bacillus polymyxa* 9A to potato seed pieces prior to planting, verticillium wilt in the resulting potato plants is substantially prevented.

*Bacillus polymyxa* 9A was deposited at the American Type Culture Collection on Dec. 27, 1983, and granted accession no. 39564.

7 Claims, No Drawings

METHOD OF USING *BACILLUS POLYMYXA* 9A TO PROTECT PLANTS AGAINST VERTICILLIUM WILT

BACKGROUND OF THE INVENTION

1. Field of the Invention

Fungal wilt diseases cause reduction in both the quality and quantity of major agricultural crops resulting in substantial economic losses each year. In particular, verticillium wilt caused by the infection of the plant's root and vascular system by *Verticillium dahliae* severly affects potatoes, cotton, and many other important crop plants. Control of *Verticillium dahliae* is problematic because of its persistence in the soil and its endophytic location in the root system of the plant. Although a number of control techniques have been suggested, such as soil fumigation, crop rotation, resistant cultivars, and use of new planting locations uninfected by the fungus, none have been entirely successful. Soil fumigation is prohibitively expensive, pollutes the environment, and must be periodically repeated. Rotation with non-susceptible crops will reduce the fungal infestation, but suitable alternate crops provide an inadequate economic return. Finally, the amount of useful farmland is limited which provides a strong disincentive to unecomonic utilization.

It would thus be desirable to provide an effective biological control which inhibits verticillium wilt in a safe and economic manner, while maintaining land productivity.

2. Description of the Prior Art

Wadi (1982) "Biological Control of *Verticillium dahliae* on Potato" (Ph.D. Thesis) Washington State University, Department of Plant Pathology, describes the use of particular strains of *Cellulomonas flavigena*, *Pseudomonas fluorescens*, and *Streptomyces flavofungini* for the control of verticillium wilt on potatoes. U.S. Department of Agriculture publication ARS-S-19 (December 1973) entitled "Verticillium Wilt of Cotton" describes various biological and chemical control schemes, including crop rotation, soil fumigation, systemic fungicides, systemic insecticides, and growth regulators. The biological control of vascular wilt fungi is discussed in Baker: "Biological Control" in *Fungal Wilt Diseases of Plants*, Chapter 14, Academic Press, New York (1981) pp. 523–561; and Kommedahl and Windels: "Introduction of Microbial Antagonists to Specific Courts of Infection: Seeds, Seedlings and Wounds" in Bettsville Symposia in Agriculture Research [5] Biological Control in Crop Production, Allanhead, Osmun, Grandida, London, Toronto, Sydney, pp. 226–248. Marois (1982) Plant Disease 66:1166–1168 describes the treatment of plant roots with *Taleromyces flavus* to treat verticillium wilt in eggplant.

SUMMARY OF THE INVENTION

A particular strain in the genus Bacillus is provided for protection of susceptible plant hosts against verticillium wilt. The subject Bacillus strain inhibits the growth of *Verticillium dahliae*, the fungus responsible for verticillium wilt, and can be used as a seed inoculant.

DESCRIPTION OF THE SPECIFIC EMBODIMENTS

*Bacillus polymyxa* 9A is provided for the inoculation of seeds to inhibit verticillium wilt. The subject strain will inhibit the growth of *Verticillium dahliae* and is not toxic when applied to the seeds of susceptible plant hosts.

*Bacillus polymyxa* 9A was deposited at the American Type Culture Collection on December 27, 1983, and granted accession no. 39564. The strain was isolated from the roots of potato plants growing in a field heavily infested with *Verticillium dahliae* Kleb., and was demonstrated to inhibit the incidence of verticillium wilt when applied to subsequently planted potato seed pieces.

The Bacillus of the present invention may be used with a variety of horticultural crops, such as tomatoes, potatoes, melons, beans, and cowpeas; field crops, such as cotton, safflower, and sunflower; fruits and nuts, such as olives, pistachios, apricots, cherries, peaches, almonds, avocadoes; and many varieties of ornamental plants. The present invention will find particular use with potatoes and cotton where the incidence of verticillium wilt is most severe.

*Bacillus polymyxa* 9A may be cultured and expanded by standard fermentation procedures. Prior to formulation, as described below, a slurry will be prepared from the culture medium, and the slurry dried onto a primary, agronomically-acceptable carrier, such as vermiculite, to form a concentrate.

The concentrate is then used to prepare a composition for application to the plant hosts. The compositions may include one or more effective Bacillus strains, and may be aqueous or non-aqueous formulations. Aqueous formulations include liquids having from about $10^5$ to $10^9$ cells/ml and pastes having $10^{10}$ cells/ml or greater. Non-aqueous formulations include dusts, wettable powders, emulsifiable concentrates, granules, and the like. The non-aqueous formulations will include agronomically-acceptable carriers, adjuvants and/or stimulants in a well known manner.

Depending on the type of formulation, the composition may be applied as a spray, dust, granule, or the like. The composition may be applied directly to the seed, or less desirably, to the soil surrounding the seed. Conveniently, the seeds may be dipped in an aqueous formulation prior to planting.

The following examples are offered by way of illustration, not by way of limitation.

EXPERIMENTAL

1. Isolation of *Bacillus polymyxa* 9A

*Bacillus polymyxa* 9A was isolated from a field of Russet Burbank potatoes in Aberdeen, Id., in which verticillium wilt, caused by *Verticillium dahliae* Kleb. (>100 propagules/g air-dried soil), was the major disease. The roots from several potato plants were removed and vigorously washed in sterile glass-distilled water and triturated in sterile mortars. The extract was serially diluted, and 0.1 ml aliquots were plated on medium 523 (Kado and Heskett (1970) Phytopathology 60:969–976). Plates were assayed for antagonists by spraying with a conidial suspension of the potato strain RB5 of *Verticillium dahliae* from a 5-day-old agar culture. The bacterium designated as 9A was purified and identified as *Bacillus polymyxa* based on criteria described in Prazmowski, A. (1880) Untersuchung uber die Entwickelungsgeschichte und Fermentwirking einiger Bacterien-Arten. Inaug. Diss., Hugo Voigt, Leipzig, pp. 1–58; Donker, H. J. L. (1926) Bijdrage tot de Kennis der Baterzuur, Butylacoholen acctonigistingen. Diss., Delft. W. D. Meinema, Delft; and Buchanan, R. E., and N. B. Biggons. (1975) Bergey's Manual of Determinative Bacteriology, 8th ed., Williams and Wilkins Company, Baltimore, Md. 12460.

*Bacillus polymyxa* 9A is a facultative anerobe, Gram variable rod, which occurs singly and sometimes in pairs. The bacterium is motile by peritrichous flagella and is a spore former. Maximum growth occurs at 43° C., while minimum growth occurs at 9° C. Growth is tolerant to 5% NaCl. Strain 9A will utilize the following as carbon sources: glucose, mannose, sucrose, lactose, arabinose, xylose, trehalose, inositol, mannitol, erythritol, sorbitol, cussinate, tartrate, and acetamide, while being unable to utilize ethanol, geraniol, citrate, butryate, proprionate and hippurate.

To further classify the strain, a series of biochemical tests were run. The results were as follows:

| Positive | Negative |
| --- | --- |
| Catalase | Cytochrome oxidase |
| Voges-proskauer | indole |
| nitrate reductase | methyl red |
| gelatin liquefaction | ureasa |
| alpha amylase | hydrogen sulfide |
| levan | dextrin |
| beta-galactosidase | gas from trehalose |
| acid from arabinose | |
| acid from xylose | |
| gas produced from glucose | |
| gas produced from lactose | |

2. Antifungal spectrum

To determine the antifungal spectrum of *Bacillus polymyxa* 9A, the bacterium was grown for 2 days at 30° C. to a diameter of 1 cm at the center of medium 523 agar plates. The plates were then oversprayed with conidial suspensions of different fungi. For those fungi which do not produce conidial growth, agar discs containing a mycelial mat of the fungus were placed on the plate opposite the bacterial patch. Antifungal activity was demonstrated by an inhibition zone appearing around the bacterial patch or between the bacterial patch and the mycelial mat of the fungus. *Baccilus polymyxa* 9A was found to inhibit the growth of the following fungi.

*Verticillium dahliae* RB5
*Verticillium dahliae* 128 (olive)
*Verticillium dahliae* Hanford (pistachio)
*Fusarium roseum* RB
*F. oxysporum fsp. vasinfectum* California strain
*Colletotrichum atramentarium* Idaho strain
*Thielaviopsis basicola* California strain
*Rhizoctonia solani* Ag3
*Phytophthora erythroseptica* California isolate
*Streptomyces scabies* (Idaho isolates)

3. Effect of various antifungal bacteria on protecting Russet Burbank potatoes against *Verticillium dahliae*

To demonstrate the protection afforded by various antifungal bacteria against verticillium wilt of potato, stems from potato plants naturally infected with *Verticillium dahliae* Kleb. were air-dried and assayed to confirm the presence of verticillium propagules. The stems were then incorporated into a standard soil mix. The bacteria being tested were grown in medium 523 broth at 30° C. to a density of $10^8$ CFU/ml, harvested by centrifugation, and suspended in sterile glass distilled water. Potato tubers were cut into seed pieces, and the seed pieces were dipped in the bacterial suspensions and planted in pots containing the soil mix which had been artificially infested with the verticillium propagules.

The pots were then placed on a greenhouse bench, and the resulting potato plants were rated for wilt incidence. Those plants treated with *Bacillus polymyxa* 9A were free from wilt, while the control plants displayed severe wilt symptoms. Potato tubers from each pot were removed and weighed. The results are set forth in Table 1.

TABLE 1

| BACTERIUM | Mean* potato weight (g) |
| --- | --- |
| *Bacillus polymyxa* 9A | 217.26 |
| *Bacillus polymyxa* 9f | 169.31 |
| *Gluconobacter oxydans* subsp. melanogenes 7 | 165.54 |
| *Pseudomonas fluorescens* 50 | 162.62 |
| *G. oxydans-melanogenes* 10 | 160.87 |
| *P. fluorescens* 80 | 158.06 |
| *Bacillus polymyxa* 5d | 150.52 |
| *Bacillus polymyxa* SJ5S4 | 149.14 |
| *Flavobacterium sp.* 60 | 146.50 |
| *Bacillus sp.* 9B | 143.31 |
| *Bacillus polymyxa* 5J3 | 139.50 |
| Control | 134.50 |
| *Bacillus sp.* 119 | 130.82 |
| *Bacillus sp.* 120 | 128.52 |
| *Bacillus polymyxa* 5d5 | 127.06 |
| *Bacillus polymyxa* 5a | 126.10 |
| *Bacillus polymyxa* 9t1 | 124.68 |
| *Bacillus laterosporus* IdaB | 112.61 |
| *Bacillus badius* SJ4R6 | 110.92 |
| *Bacillus badius* 20 | 96.44 |

*Data tested by Duncan's multiple range test for variable: Y. This test controls error rates at different levels depending on the number of means between each pair being compared. Its operating characteristics somewhat resemble Fisher's unprotected LSD Test. Alpha = 0.05; DF = 57; MSE = 3143.77. Some samples were zero value and these were included.

The above-desscribed procedure was followed to determine the effect of various antifungal bacteria on wilt control and yield of potatoes in the field. The bacterial inoculum contained $10^{11}$ CFM/ml, and the bacterial-treated seed pieces were planted by hand in a field naturally infested with Verticillium propagules. The results, measured yield per acre at the end of the growing season, are set forth in Table 2. It was also found that the plants treated with *Bacillus polymyxa* 9A yielded an average of 134 Baker premium grade potatoes (large size, free of cracks and blemishes) per acre, while the control plants produced only 85 Baker premium grade potatoes per acre.

TABLE 2

| BACTERIUM | Mean* number of sacks per acre |
| --- | --- |
| *Bacillus polymyxa* 9A | 345.57 |
| *Bacillus sp.* 119 | 300.12 |
| *P. fluorescens* 80 | 294.62 |
| *Bacillus polymyxa* 9f | 286.20 |
| *Flavobacterium* 60 | 284.67 |
| *Bacillus polymyxa* 5J3 | 282.85 |
| *Bacillus polymyxa* 5a | 273.25 |
| *G. oxydans* 7 | 262.65 |
| *Bacillus polymyxa* 9t1 | 260.92 |
| *Bacillus polymyxa* 5d5 | 254.55 |
| *Bacillus badius* 20 | 252.50 |
| *G. oxydans* 10 | 251.62 |
| *P. fluorescens* 50 | 250.50 |
| *Bacillus polymyxa* 5d | 241.75 |
| *Bacillus sp.* 120 | 240.60 |
| Control | 240.02 |
| *Bacillus sp.* 9b | 237.25 |
| *Bacillus polymyxa* SJ5S4 | 236.37 |
| *Bacillus laterosporus* IdaB | 235.37 |

TABLE 2-continued

| BACTERIUM | Mean* number of sacks per acre |
|---|---|
| Bacillus badius SJ4R6 | 201.07 |

*Duncan's multiple range test for variable: Y. This test controls error rates at different levels depending on the number of means between each pair being compared. Its operating characteristics somewhat resemble Fisher's unprotected LSD test. Alpha = 0.05; DF = 57; and MSE = 2752.61

4. Effect of soil temperature on persistence of *Bacillus polymyxa* 9A

Minimum and maximum growth temperatures of isolate 9A were determined by streaking the bacteria on medium 523 agar plates, and incubating the plates at different temperatures ranging from 0° C. to 70° C.

Soil temperatures during the growing season were determined by thermometers inserted at different depths in the soil. At a depth of 6 inches, soil temperature was found to be 26° C. for untarped soil and 41° C. for plastic (2 mil clear) tarped soil.

To determine the effect of soil temperature on bacterial populations, soil samples from both uncovered and tarped locations were removed with a soil probe. The samples were mixed with sterile glass-distilled water, and a dilution series was plated on agar medium 523 in petri plates. After incubation for 48 hours at 30° C., the number of bacteria grown on each plate was counted and their types were determined based on morphological, physiological and biochemical tests. For untarped soil, few Gram negative bacteria were present, while a greater number of Bacillus species were present. For tarped soil, the number of Bacillus species doubled, while Gram negative species were undetectable. Thus, elevating the soil temperature, either by covering, using a greenhouse, or any other technique, will encourage the growth and survival of *Bacillus polymyxa* 9A and promote biological control of verticillium wilt.

In accordance with the present invention, Bacillaceae are provided which confer protection from *Verticillium dahliae* which causes verticillium wilt. By inoculating seeds with the Bacillaceae of the present invention, substantial improvements in the quality and quantity of the resulting crops can be achieved.

Although the foregoing invention has been described in some detail by way of illustration and example for purposes of clarity of understanding, it will be obvious that certain changes and modifications may be practiced within the scope of the appended claims.

What is claimed is:

1. A method for inhibiting verticillium wilt on a susceptible host plant, said method comprising applying an effective amount of *Bacillus polymyxa* 9A, which has been designated A.T.C.C. accession number 39564.

2. A method as in claim 1, wherein the *Bacillus polymyxa* 9A are applied to seeds of the plant host prior to planting.

3. A method as in claim 1, wherein the *Bacillus polymyxa* 9A are applied to the soil prior to planting.

4. A method as in claim 1, wherein the host plant is a potato plant.

5. A method for protecting a host plant against verticillium wilt, said method comprising inoculating the seed of said host plant with *Bacillus polymyxa* 9A, which has been designated A.T.C.C. accession number 39564, prior to planting said seed in soil.

6. A method as in claim 5, wherein the seed is inoculated by applying said *Bacillus polymyxa* 9A as an aqueous suspension.

7. A method as in claim 5, wherein the seed is a potato piece.

* * * * *